(12) United States Patent
Vennestøm et al.

(10) Patent No.: US 10,933,408 B2
(45) Date of Patent: *Mar. 2, 2021

(54) CATALYST COMPRISING A MOLECULAR SIEVE BELONGING TO THE ABC-6 FRAMEWORK FAMILY WITH DISORDER IN THE ABC STACKING SEQUENCE AND USE OF THE CATALYST

(71) Applicant: Umicore AG & Co. KG, Hanau-Wolfgang (DE)

(72) Inventors: Peter N. R. Vennestøm, Virum (DK); Lars Fahl Lundegaard, Roskilde (DK); Brian Jensen, Espergærde (DK)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/335,345

(22) PCT Filed: Nov. 2, 2017

(86) PCT No.: PCT/EP2017/078024
§ 371 (c)(1),
(2) Date: Mar. 21, 2019

(87) PCT Pub. No.: WO2018/086977
PCT Pub. Date: May 17, 2018

(65) Prior Publication Data
US 2019/0217280 A1  Jul. 18, 2019

(30) Foreign Application Priority Data
Nov. 10, 2016  (DK) .................................. 2016 00700

(51) Int. Cl.
*B01J 29/70* (2006.01)
*B01D 53/94* (2006.01)
(Continued)

(52) U.S. Cl.
CPC ............ *B01J 29/76* (2013.01); *B01D 53/565* (2013.01); *B01D 53/945* (2013.01);
(Continued)

(58) Field of Classification Search
CPC ..... C01B 39/026; C01B 39/305; C01B 39/48; C01P 2002/72; B01J 29/56; B01J 29/70;
(Continued)

(56) References Cited

U.S. PATENT DOCUMENTS 4,508,837 A * 4/1985 Zones ...................... B01J 29/04
423/326
5,248,491 A * 9/1993 Skeels ..................... C01B 39/48
423/705
(Continued)

FOREIGN PATENT DOCUMENTS

EP      1 204 592 A1   5/2002
WO   WO 01/09037 A1   2/2001

OTHER PUBLICATIONS

Dent et al "Crystal Structure of Chabazite, a Molecular Sieve", NATURE, vol. 181 pp. 1794-1796 (Year: 1958).*
(Continued)

*Primary Examiner* — David M Brunsman
(74) *Attorney, Agent, or Firm* — Blank Rome LLP

(57) ABSTRACT

Catalyst and use of the catalyst comprising a molecular sieve belonging to the ABC-6 framework family with disorder in the ABC stacking sequence essentially composed of double-six-ring periodic building units and having a mole ratio of silicon oxide to aluminum oxide from about 8 to about 60.

20 Claims, 8 Drawing Sheets

(51) Int. Cl.

| | | |
|---|---|---|
| *B01J 29/76* | (2006.01) | |
| *C01B 39/02* | (2006.01) | |
| *B01J 29/74* | (2006.01) | |
| *C07C 1/20* | (2006.01) | |
| *B01D 53/56* | (2006.01) | |
| *B01J 37/00* | (2006.01) | |
| *B01J 37/06* | (2006.01) | |
| *B01J 37/08* | (2006.01) | |
| *C01B 39/04* | (2006.01) | |
| *C07C 29/48* | (2006.01) | |
| *C07C 41/01* | (2006.01) | |
| *B01J 37/02* | (2006.01) | |

(52) U.S. Cl.
CPC ..... *B01D 53/9418* (2013.01); *B01D 53/9427* (2013.01); *B01D 53/9436* (2013.01); *B01D 53/9445* (2013.01); *B01J 29/70* (2013.01); *B01J 29/74* (2013.01); *B01J 29/743* (2013.01); *B01J 29/763* (2013.01); *B01J 37/009* (2013.01); *B01J 37/0018* (2013.01); *B01J 37/06* (2013.01); *B01J 37/08* (2013.01); *C01B 39/023* (2013.01); *C01B 39/026* (2013.01); *C01B 39/04* (2013.01); *C07C 1/20* (2013.01); *C07C 29/48* (2013.01); *C07C 41/01* (2013.01); *B01D 2255/102* (2013.01); *B01D 2255/20738* (2013.01); *B01D 2255/20761* (2013.01); *B01D 2255/50* (2013.01); *B01J 37/0246* (2013.01); *B01J 2229/186* (2013.01); *C01P 2002/72* (2013.01); *C01P 2004/03* (2013.01); *C07C 2529/70* (2013.01); *C07C 2529/74* (2013.01); *C07C 2529/76* (2013.01)

(58) Field of Classification Search
CPC . B01J 29/76; B01J 29/763; B01J 29/74; B01J 29/743; B01D 53/9418; B01D 2255/50; B01D 53/945; C07C 11/02; C07C 31/04; C07C 41/01; C07C 2529/70; C07C 2529/74; C07C 2529/76

See application file for complete search history.

(56) References Cited

U.S. PATENT DOCUMENTS

| | | | | |
|---|---|---|---|---|
| 6,254,849 | B1 * | 7/2001 | Lee ........................ | B01D 53/02 423/706 |
| 8,809,217 | B2 * | 8/2014 | Andersen ............... | B01J 29/005 502/60 |
| 9,796,596 | B2 * | 10/2017 | Liu ........................ | C01B 39/48 |

OTHER PUBLICATIONS

"Internal-Combustion Engine", Encyclopedia Britannica, Downloaded Jun. 16, 2020 (Year: 2020).*
D. Xie et al., "SSZ-52, A Zeolite with an 18-Layer Aluminosilicate Framework Structure Related to That of the DeNOx Catalyst Cu-SSZ-13", Journal of the American Chemical Society, American Chemical Society, US., vol. 135, No. 28, Jul. 17, 2013, pp. 10519-10524.
R. Szostak et al., "Babelite: The Random Member of the ABC-D6R Family of Zeolites", Journal of the Chemical Society, Chemical Communications, No. 20, Jan. 1, 1994, pp. 2357-2358.
G. W. Skeels et al., "Synthesis and Characterization of Phi-Type Zeolites LZ-276 and LZ-277: Faulted Members of the ABC-D6R Family of Zeolites", Microporous and Mesoporous Mater, vol. 30, No. 2-3, Sep. 1, 1999, pp. 335-346.
T. Willhammar et al., "Stacking Disorders in Zeolites and Open-Frameworks—Structure Elucidation and Analysis by Electron Crystallography and X-ray Diffraction", Zeitschrift Für Kristallographie—Crystalline Materials, vol. 228, No. 1, Jan. 1, 2013, pp. 11-27.
J. Plévert et al., "Faulting Effects in the CHA-GME Group of ABC-6 Materials", Proceedings of the International Zeolite Conference, Jan. 1, 1998, pp. 2445-2452.

* cited by examiner

CATALYST COMPRISING A MOLECULAR SIEVE BELONGING TO THE ABC-6 FRAMEWORK FAMILY WITH DISORDER IN THE ABC STACKING SEQUENCE AND USE OF THE CATALYST

This application is a 371 filing of PCT/EP2017/078024, filed Nov. 5, 2017.

The present invention relates to a catalyst comprising a molecular sieve belonging to the ABC-6 framework family with disorder in the ABC stacking sequence.

In particular, the invention is a catalyst comprising a crystalline molecular sieve material belonging to the ABC-6 framework family with disorder in the ABC stacking sequence essentially composed of double-six-ring periodic building units with a high silica-to-alumina ratio and the use of the catalyst in chemical reactions.

Zeolites are crystalline *Microporous* materials formed by corner-sharing $TO_4$ tetrahedra (T=Si, Al, P, Ge, B, Ti, Sn, etc.), interconnected by oxygen atoms to form pores and cavities of uniform size and shape precisely defined by their crystal structure. Zeolites are also denoted "molecular sieves" because the pores and cavities are of similar size as small molecules. This class of materials has important commercial applications as absorbants, ion-exchangers and catalysts.

Molecular sieves are classified by the International Zeolite Association (IZA) according to the rules of the IUPAC Commission on Molecular Sieve Nomenclature. Once the topology of a new framework is established, a three letter code is assigned. This code defines the atomic structure of the framework, from which a distinct X-ray diffraction pattern can be described.

There are a large number of molecular sieve structures known today. Some known molecular sieves belong to certain families of structures with similar features. One specific family, the ABC-6 family, can be described as a stacking of two-dimensional periodic layers of non-connected planar 6-ring motifs, made up from 6 T-atoms (T=Si, Al etc.) connected by oxygen atoms. The resulting layer with hexagonal symmetry is also called the periodic building unit (PerBU).

The stacking is typically described by a sequence of letters "A", "B" and "C" that indicates the relative positions of neighboring layers. "A", "B" and "C" refers to the well-known relative positions of neighboring layers when stacking hexagonal layers of close packed spheres. Once the repeating stacking sequence is known, the 3-dimensional framework topology is defined. Well-known examples of framework topologies that belong to the ABC-6 family are CAN (stacking sequence AB . . . ), SOD (stacking sequence ABC . . . ). In these examples the structure is constructed only of single 6-rings. Once there is a repetition of A, B or C in the stacking sequence, double-6-rings appear. Well known framework topologies with double-6-rings in the structure are GME (stacking sequence: AABB . . . ) and CHA (stacking sequence AABBCC . . . ). In a similar manner a framework topology can also consist of both single-6-rings and double-6-rings. Well-known examples include OFF (stacking sequence: AAB . . . ) and ERI (stacking sequence: AABAAC . . . ).

With respect to the present invention it is useful to discuss as an example the specific framework topologies CHA and GME. The CHA and GME framework topologies are both well-defined ordered structures. The CHA framework topology is a small-pore material characterized by a three-dimensional 8-membered-ring pore systems containing double-six-rings (d6R) and cha cages. The GME framework topology is a large-pore material characterized by 12-membered-ring channels in one dimension and 8-membered ring pore systems in the other two dimensions containing double-six-rings (d6R) and gme cages.

Any finite sequence of A, B and C layers, stacked periodically, forms an ordered structure with well-defined unit cells in all three spatial dimensions. Any non-periodic mistake in the stacking sequence will lead to a disordered structure without a well-defined periodic unit cell in the direction normal to the layers. When sufficient stacking disorder occurs the material can no longer be considered to have the same framework topology as the ordered framework. As a consequence of disorder in the ABC-6 sequence, different local topological features arise such as a distribution of different cage-sizes that are completely different to the ordered parent framework topology. This will lead to different adsorption, diffusion and material properties, in particular catalytic properties.

As an example, CHA and GME topologies both consist of a sequence of double 6-ring layers. Each layer is shifted ⅓ of the periodicity relative to the previous layer. In case of CHA the ⅓ shift consistently happens in the same direction, which means that after three steps the layer has shifted a full periodicity relative to the first layer. In case of GME the ⅓ shift consistently happens in alternating directions, which means that after two steps the layer is back to the original position. The simplest way of describing the amount of disorder in the CHA-GME series is to define the choice of changing stacking direction (faulting) to a simple probability. This means a faulting probability of 0% results in pure ordered CHA, while a probability of 100% results in pure ordered GME. In the following description, this specific percentage is used to describe the amount of disorder in the molecular sieve. In reality, the probability of changing stacking direction will be slightly dependent on stacking directions of previous steps, because of relaxation effects. For this reason, the above explanation using a faulting probability in its simplest form should not be used to limit the invention disclosed herein.

X-ray diffraction patterns of the stacking disordered CHA-GME series can be simulated using DIFFaX [M. M. J. Treacy, J. M. Newsam & M. W. Deem 1991 "A General Recursion Method for Calculating Diffracted Intensities from Crystals Containing Planar Faults" Proc. Roy. Soc. Lond. A433, 499-520], available from [http://www.public.asu.edu/~mtreacy/DIFFaX.html]. The simulated patterns can be used for comparison with experimentally measured X-ray diffraction data to elucidate the approximate amount of disorder in prepared materials.

X-ray diffraction patterns with increments of 10% stacking disorder are shown in FIG. 1. As mentioned above, a faulting probability of 0% corresponds to pure CHA while a faulting probability of 100% corresponds to pure GME There are a number of reported examples in the literature for the preparation and use of materials described as disordered ABC 6-ring molecular sieves with disorder in the 6-ring stacking sequence. Disordered materials only containing double-6-rings are typically described as part of the disordered CHA-GME series.

So far, the known molecular sieves that have been synthesized and identified as members of the disordered CHA-GME series are: Babelite [R. Szostak and K. P. Lillerrud, J. Chem. Soc. Chem. Commun. 1994(20), 2357 (1994)]; Linde D [K. P. Lillerud, R. Szostak and A. Long, J. Chem. Soc. Faraday Trans. 90, 1547 (1994); GB Patent 868,646]; Phi [K. P. Lillerud, R. Szostak and A. Long, J. Chem. Soc.

Faraday Trans. 90, 1547 (1994); U.S. Pat. No. 4,124,686]; ZK-14 [G. H. Kuehl. In: Molecular Sieves. S.C.I., London, 1967, p 85]; LZ-276 [G. W. Skeels, M. Sears, C. A. Bateman, N. K. McGuire, E. M. Flanigen, M. Kumar, R. M. Kirchner, Micropor. Mesopor. Mater. 30, 335 (1999); U.S. Pat. No. 5,248,491]; LZ-277 [G. W. Skeels, M. Sears, C. A. Bateman, N. K. McGuire, E. M. Flanigen, M. Kumar and R. M. Kirchner, Micropor. Mesopor. Mater. 30, 335 (1999); U.S. Pat. No. 5,192,522].

In the case of Babelite, the material is said to crystallize with similar $SiO_2/Al_2O_3$ ratios as the synthetic Chabazite that are typically close to 4.0 [Verified Syntheses of Zeolitic Materials, 2nd Revised Edition, Harry Robson, editor, Karl Petter Lillerud, XRD Patterns (2001) ISBN: 0-444-50703-5]. The highest reported $SiO_2/Al_2O_3$ ratio of Linde D is 4.9. U.S. Pat. No. 4,124,686 discloses zeolite Phi to have a $SiO_2/Al_2O_3$ ratio of 4.6. As to LZ-277, U.S. Pat. No. 5,192,522 discloses a maximum $SiO_2/Al_2O_3$ ratio of 6.6. Of all the known materials LZ-276 has been reported with the highest $SiO_2/Al_2O_3$ ratios where U.S. Pat. No. 5,248,491 discloses a $SiO_2/Al_2O_3$ ratio of 7.7 and Skeels et al. report a $SiO_2/Al_2O_3$ ratio of 7.8 when exploring the synthesis of LZ-276. In the preparation of LZ-276 tetraethylorthosilicate is used as the sole source of silicon, and sodiumaluminate is used as the sole source of Al. The resulting morphology of LZ-276 is later reported to be spherical intergrowths of disc-shaped particles [G. W. Skeels, M. Sears, C. A. Bateman, N. K. McGuire, E. M. Flanigen, M. Kumar, R. M. Kirchner, Micropor. Mesopor. Mater. 30, 335 (1999)].

It is commonly acknowledged in the art that the hydrothermal stability of aluminosilicate molecular sieves become higher when the $SiO_2/Al_2O_3$ ratio is increased. Consequently, there is a need to increase the $SiO_2/Al_2O_3$ ratios of the known molecular sieve materials, in particular for applications where hydrothermal stability is an issue.

Furthermore, the specific amount of disorder in zeolites belonging to the ABC-6 family dictates specific topological features, such as distribution of cages with various dimensions, and ultimately catalytic and diffusion properties of such molecular sieves.

To the best of our knowledge, there are no reports on the possibility to control the amount of disorder when preparing disordered molecular sieve materials.

Accordingly, there is a strong desire to provide a catalyst comprising disordered ABC 6-ring molecular sieves with a high mole ratio of silicon oxide to aluminum oxide.

Thus, the invention is in first aspect a catalyst comprising a molecular sieve belonging to the ABC-6 framework family with disorder in the ABC stacking sequence essentially composed of double-six-ring periodic building units and having a mole ratio of silicon oxide to aluminum oxide from about 8 to about 60.

Specific features and embodiment of the invention either used alone or in combination thereof are listed below.

In one embodiment, the calcined form of the molecular sieve in the catalyst has a powder X-ray diffraction pattern collected in Bragg-Brentano geometry with a variable divergence slit using Cu K-alpha radiation essentially as shown in the following Table:

| 2-Theta (°) | d-spacing (Å) | Relative peak area | Peak character |
|---|---|---|---|
| 7.45-7.54 | 11.85-11.72 | W-M | Broad to sharp |
| 9.55-9.65 | 9.24-9.15 | VS-W | Sharp to broad |
| 11.40-11.66 | 7.75-7.58 | W-M | Broad to sharp |

-continued

| 2-Theta (°) | d-spacing (Å) | Relative peak area | Peak character |
|---|---|---|---|
| 12.90-13.04 | 6.85-6.78 | VS-M | Sharp |
| 14.07-14.21 | 6.29-6.23 | W | Sharp to broad |
| 14.89-15.12 | 5.94-5.85 | W | Broad to sharp |
| 16.08-16.27 | 5.50-5.44 | VS-W | Sharp to broad |
| 17.17-17.34 | 5.16-5.11 | W-S | Broad to sharp |
| 17.71-18.00 | 5.00-4.92 | VS-M | Sharp | where the relative areas of the observed peaks in the 2-Theta range 7-19 degrees are shown according to: W=weak: 0-20%; M=medium: 20-40%; S=strong: 40-60% and VS=very strong: 60-100%.

In further an embodiment, the molecular sieve belonging to the ABC-6 framework family with disorder in the ABC stacking sequence belongs to the disordered CHA-GME series.

In still an embodiment, the amount of stacking disorder of the molecular sieve is between 1 and 99%.

In an embodiment, crystals of the molecular sieve have a bipyramidal, elongated bipyramidal or capped bipyramidal morphology.

In another embodiment, the silica-to-alumina mole ratio of the molecular sieve is between 8 and 40.

In a preferred embodiment, the silica-to-alumina mole ratio is between 10 and 20.

In a further embodiment, at least a part of the aluminum and/or silicon in the molecular sieve is substituted by one or more metals selected from tin, zirconium, titanium, hafnium, germanium, boron, iron, indium and gallium.

In another embodiment, the catalyst molecular sieve of the catalyst comprises copper and/or iron.

A further aspect of the invention is use of the catalyst in specific catalytic reactions.

Specific embodiments of the use of the catalyst are the following.

One embodiment is a method for the conversion of nitrogen oxides to nitrogen in presence of a reductant comprising the step of contacting the nitrogen oxides and the reductant with the catalyst according to any one of the above embodiments of the catalyst.

In a preferred embodiment of the above method, the reductant comprises hydrocarbons and/or ammonia or a precursor thereof.

In a further embodiment of the above method for the conversion of nitrogen oxides to nitrogen, the nitrogen oxides are contained in engine exhaust.

In still an embodiment of the above method for the conversion of nitrogen oxides to nitrogen, the nitrogen oxides are contained in exhaust from a gas turbine.

In another embodiment of the above method for the conversion of nitrogen oxides to nitrogen, the nitrogen oxides comprise nitrous oxide.

In further an embodiment, the catalyst is used in a method for the selective oxidation of ammonia to nitrogen a comprising the step of contacting the ammonia with the catalyst.

In an embodiment, the catalyst is used in the above method for the selective oxidation of ammonia to nitrogen is combined with an oxidation functionality.

In still an embodiment, the catalyst is used in the above method for the selective oxidation of ammonia to nitrogen, the catalyst is located downstream of a selective catalytic reduction catalyst wherein an excess of ammonia is used to reduce nitrogen oxides.

Another embodiment of the use of the catalyst, is a method for the simultaneous oxidation of hydrocarbons, carbon monoxide and reduction of nitrogen oxides comprising the step of contacting the hydrocarbons, carbon monoxide and the nitrogen oxides with the catalyst.

In an embodiment of the method for the simultaneous oxidation of hydrocarbons, carbon monoxide and reduction of nitrogen oxides, the molecular sieve of the catalyst comprises one or more platinum group metals.

Another embodiment of the use of the catalyst is a method for the conversion of oxygenates to hydrocarbons comprising the step of contacting the oxygenates with the catalyst.

In an embodiment of the method for the conversion of oxygenates to hydrocarbons, the hydrocarbons produced are mainly olefins.

Another embodiment of the use of the catalyst, is a method for partial oxidation of methane to methanol and/or dimethyl ether comprising the step of contacting the methane with the catalyst.

Figure 1:
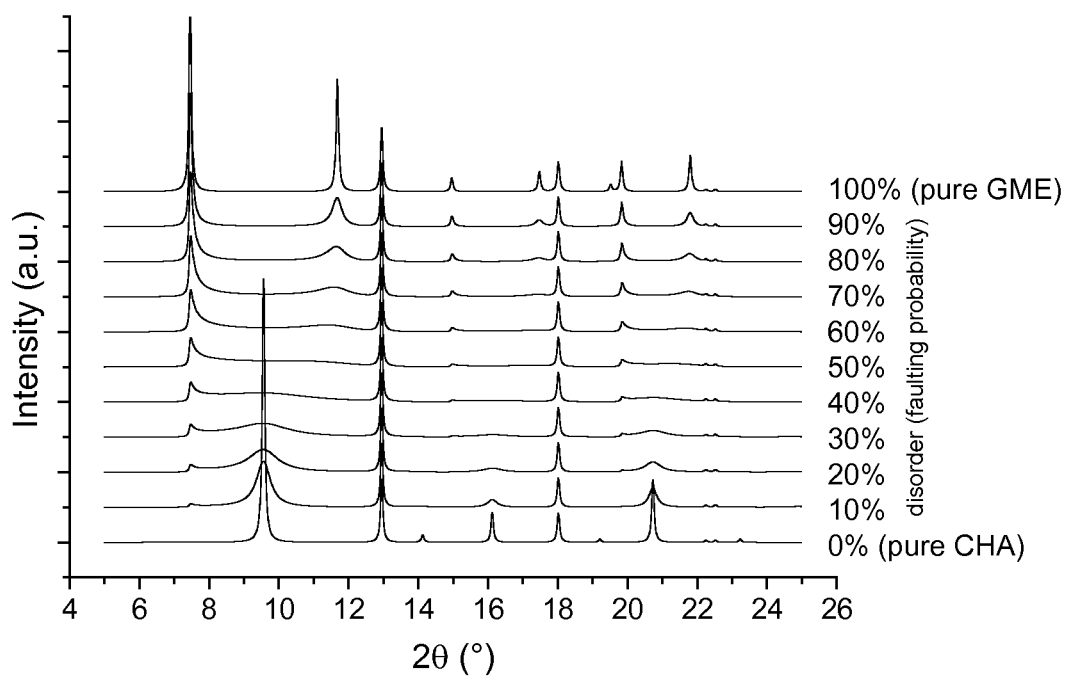
FIG. 1 is Simulated XRPD patterns from DIFFaX of the stacking disordered CHA-GME series.

The term framework type or framework topology as used herein, refers to the unique atomic structure of a specific molecular sieve, named by a three letter code devised by the International Zeolite Association [Atlas of Zeolite Framework Types, 6th revised edition, 2007, Ch. Baerlocher, L. B. McCusker and D. H. Olson, ISBN: 978-0-444-53064-6]. When stacking disorder occurs, the material cannot be described by a single well-defined unit cell and it is therefore non-periodic in one or more dimensions. Herein, this type of material is referred as disordered materials or as materials with disorder in the stacking sequence. Materials of this type are well-known to a person skilled in the art and are often also referred to as intergrowth structures. Specifically, materials belonging to the stacking disordered CHA-GME series are often also be described as intergrowths of the two end-member framework topologies.

In the preparation of the novel molecular sieve comprised of the catalyst according to the invention, belonging to the ABC-6 framework family with disorder in the ABC stacking sequence essentially composed of double-six-ring periodic building units with high silica-to-alumina ratios, at least an organic structure directing agent (OSDA) in combination with at least some amount of a crystalline molecular sieve with 6-rings contained in the structure is used. The OSDA is a cation with the generic structure described as $[NR^1R^2R^3R^4]^+$, wherein at least three of the R-groups are linear alkyl groups with one to four carbon atoms.

The OSDA cations are associated with anions, which can be hydroxide, chloride, bromide, iodide etc. as long as they are not detrimental to the formation of the molecular sieve.

The novel molecular sieve is typically prepared by forming 1) a mixture comprising at least the OSDA, a crystalline molecular sieve, a source of alkali or earth alkali, hydroxide ions and water. Optionally an additional source of silicon and an additional source aluminium or a source of both silicon and aluminium is used 2) exposing the mixture to conditions capable of crystallizing the molecular sieve and 3) separating the molecular sieve product.

The overall molar composition of the synthesis mixture from which the molecular sieve product can be synthesized is provided in Table 1.

TABLE 1

| Component | Broad range | Preferred range |
|---|---|---|
| SiO2/Al2O3 | 8-60 | 10-40 |
| OSDA/SiO2 | 0.01-1.0 | 0.05-0.60 |
| A/SiO2 | 0.01-1.0 | 0.05-0.60 |
| OH/SiO2 | 0.01-1.5 | 0.1-1.2 |
| H2O/SiO2 | 2-200 | 5-100 |

Examples of crystalline molecular sieves that can be used include FAU, GME, LEV, AEI, LTA, OFF, CHA and ERI type molecular sieves.

Examples of OSDAs include the following cations: tetraethylammonium, methyltriethylammonium, propyltriethylammonium, diethyldipropylammonium, diethyldimethylammonium, choline etc.

Preferably, tetraethylammonium is used in the method according to the invention.

Optional additional sources of aluminium include oxides and salts, such as alumina, boehmite, aluminates, hydroxides, chlorides, nitrates, sulfates etc.

Optional additional sources of silicon include oxides, salts and alkoxides, such as silica, fumed silica, silicic acid, silicates, colloidal silica, tetraalkyl orthosilicates etc.

Optional additional sources of both silicon and aluminium include oxides, clays and previously synthesized materials such as precipitated silica-alumina, amorphous silica-alumina, kaolin, ordered mesoporous materials etc.

Other tetravalent elements can also be introduced into the synthesis mixture. Such elements include tin, zirconium, titanium, hafnium, germanium and combinations thereof.

Trivalent elements can also be included into the synthesis mixture either together with aluminium or without the presence of aluminium. Such trivalent elements include boron, iron, indium, gallium and combinations thereof. Both tetravalent and trivalent elements may be added in the form of metals, salts, oxides, sulphides and combinations thereof.

Transition metals can be included in the synthesis mixture either as simple salts or as complexes that protects the transition metal from precipitation under the caustic conditions dictated by the synthesis mixture. Especially, polyamine complexes are useful for protecting transition metal ions of copper and iron during preparation and can also act to direct the synthesis towards specific molecular sieves (see for example the use of polyamines in combination with copper ions in US Patent application 2016271596). In such a way transition metal ions can be introduced into the interior of the molecular sieve already during crystallization.

The synthesis mixture can also contain inexpensive pore-filling agents that can help in the preparation of more siliceous products. Such pore filling agents could be crown-ethers, simple amines and other uncharged molecules.

The synthesis mixture can also comprise seed crystals of molecular sieves. Molecular sieve crystals belonging to the ABC-6 family are preferred such as CHA, GME or molecular sieves belonging to the disordered CHA-GME series. The amount of seed crystals can vary from 0.1 to 25% based on the total amount of silica in the synthesis mixture.

It was further observed that the presence of crystalline molecular sieves in the synthesis mixture makes it possible to extend the composition of the prepared product to higher silica-to-alumina ratios compared to what is possible with traditional sources of silicon and aluminium. As already mentioned above, the highest silica-to-alumina ratio for a disordered CHA-GME type molecular sieve is for LZ-276, which has a reported silica-to-alumina ratio of 7.7-7.8 [U.S. Pat. No. 5,248,491; G. W. Skeels, M. Sears, C. a. Bateman, N. K. McGuire, E. M. Flanigen, M. Kumar, R. M. Kirchner, *Microporous* Mesoporous Mater. 1999, 30, 335-346.] and a morphology described as spherical intergrowths of disc-shaped particles, which may not be useful in several applications, whereas the morphology of the crystals prepared by the method according to invention is bipyramidal, elongated bipyramidal or capped bipyramidal.

The amount of stacking disorder is controlled by variation of the amount of OSDA, alkali and hydroxide in the synthesis mixture. By variation of the composition of the synthesis mixture, the amount of stacking disorder in the obtained molecular sieve product can be varied from about 1% to about 99%.

Crystallization of the synthesis mixture to form the novel molecular sieve is performed at elevated temperatures until the molecular sieve is formed. Hydrothermal crystallization is usually conducted in a manner to generate an autogenous pressure at temperatures from 100-200° C. in an autoclave and for periods of time between two hours and 20 days. The synthesis mixture can be subjected to stirring during the crystallization.

Once the crystallization has completed, the resulting solid molecular sieve product is separated from the remaining liquid synthesis mixture by conventional separation techniques such as decantation, (vacuum-) filtration or centrifugation. The recovered solid crystals are then typically rinsed with water and dried using conventional methods (e.g. heating to 75-150° C. under atmospheric pressure, vacuum drying or freeze-drying etc.) to obtain the 'as-synthesized' molecular sieve. The 'as-synthesized' product refers to the molecular sieve after crystallization and prior to removal of the structure directing agent(s) or other organic additives. The typical composition of the molecular sieve, in its anhydrous state, obtained by the process according to the invention, is summarized in Table 2.

TABLE 2

| Component | Broad range | Preferred range |
| --- | --- | --- |
| SiO2/Al2O3 | 8-60 | 8-40 |
| OSDA/SiO2 | 0.01-0.5 | 0.05-0.40 |
| A/SiO2 | 0.01-0.5 | 0.05-0.40 |

The molecular sieve prepared by the above described method belongs to the ABC-6 framework family with disorder in the ABC stacking sequence, essentially composed of double-six-ring periodic building units.

Its as-synthesized form is characterized by X-ray diffraction pattern, which will vary with the amount of stacking disorder in the molecular sieve. The X-ray diffraction pattern together with the possible variations expressed by the peak character are summarized in Table 3 Table 3 and are representative for the as-synthesized product.

TABLE 3

Characteristic powder X-ray diffraction peaks for the as-synthesized molecular sieve

| 2-Theta (°) [Cu Kalpha] | d-spacing (Å) [Cu Kalpha] | Relative peak area[a] | Peak character[b] |
| --- | --- | --- | --- |
| 7.45-7.54 | 11.85-11.72 | W-M | Broad to sharp |
| 9.55-9.65 | 9.24-9.15 | VS-W | Sharp to broad |
| 11.40-11.66 | 7.75-7.58 | W-M | Broad to sharp |
| 12.90-13.04 | 6.85-6.78 | S-W | Sharp |
| 14.07-14.21 | 6.29-6.23 | M-W | Sharp to broad |
| 14.89-15.12 | 5.94-5.85 | W | Broad to sharp |
| 16.08-16.27 | 5.50-5.44 | VS-W | Sharp to broad |
| 17.17-17.34 | 5.16-5.11 | W-S | Broad to sharp |
| 17.71-18.00 | 5.00-4.92 | VS-S | Sharp |

[a]Relative areas of the observed peaks in the 2-Theta range 7-19 degrees: W = weak: 0-20%; M = medium: 20-40%; S = strong: 40-60% and VS = very strong: 60-100%. Collected in Bragg-Bren-tano geometry with variable divergence slit (10 mm sample length).
[b]The relative peak area and the peak character is described as going from the CHA end-member when increasing the amount of stacking disorder.

The organic molecules still retained in the as-synthesized molecular sieve are in most cases, unless used in the as-synthesized form, removed by thermal treatment in the presence of oxygen. The temperature of the thermal treatment should be sufficient to remove the organic molecules either by evaporation, decomposition, combustion or a combination thereof. Typically, a temperature between 150 and 750° C. for a period of time sufficient to remove the organic molecule(s) is applied. A person skilled in the art will readily be able to determine a minimum temperature and time for this heat treatment. Other methods to remove the organic material(s) retained in the as-synthesized molecular sieve include extraction, vacuum-calcination, photolysis or ozone-treatment.

The X-ray diffraction pattern together with the possible variations in the peak character from the varying amount of stacking disorder are summarized in Table 4 and are representative for the calcined product prepared by the method according to the invention and after calcination.

TABLE 4

Characteristic powder X-ray diffraction peaks of the calcined molecular sieve

| 2-Theta (°) [Cu Kalpha] | d-spacing (Å) [Cu Kalpha] | Relative peak area[a] | Peak character[b] |
|---|---|---|---|
| 7.45-7.54 | 11.85-11.72 | W-M | Broad to sharp |
| 9.55-9.65 | 9.24-9.15 | VS-W | Sharp to broad |
| 11.40-11.66 | 7.75-7.58 | W-M | Broad to sharp |
| 12.90-13.04 | 6.85-6.78 | VS-M | Sharp |
| 14.07-14.21 | 6.29-6.23 | W | Sharp to broad |
| 14.89-15.12 | 5.94-5.85 | W | Broad to sharp |
| 16.08-16.27 | 5.50-5.44 | VS-W | Sharp to broad |
| 17.17-17.34 | 5.16-5.11 | W-S | Broad to sharp |
| 17.71-18.00 | 5.00-4.92 | VS-M | Sharp |

[a]Relative areas of the observed peaks in the 2-theta range 7-19 degrees: W = weak: 0-20%; M = medium: 20-40%; S = strong: 40-60% and VS = very strong: 60-100%. Collected in Bragg-Brentano geometry with variable divergence slit (10 mm sample length).
[b]The relative peak area and the peak character is described as going from the CHA end-member when increasing the amount of stacking disorder.

It is typically desirable to remove the remaining alkali or earth alkali ions (e.g. $Na^+$) from the molecular sieve by ion-exchange or other known methods. Ion-exchange with ammonium and/or hydrogen are well recognized methods to obtain the $NH_4$-form or H-form of the molecular sieve. Metal ions may also be included in the ion-exchange procedure or introduced separately. The $NH_4$-form of the material can be converted to the H-form by simple heat treatment in a similar manner as described above.

In certain cases, it may be desirable to alter the chemical composition of the obtained molecular sieve, such as altering the silica-to-alumina ratio. Without being bound by any order of the post-synthetic treatments, acid leaching (inorganic and organic using complexing agents such as EDTA etc. can be used), steam-treatment, desilication and combinations thereof or other methods of demetallation can be useful in this case.

To promote specific catalytic applications as disclosed hereinbefore, specific metals can be introduced into the novel molecular sieve to obtain a metal-substituted, metal-impregnated or metal-exchanged molecular sieve. The metals are introduced as metal ions by ion-exchange, impregnation, solid-state procedures and other known techniques. Metals can be introduced to yield essentially atomically dispersed metal ions or be introduced to yield small clusters or nanoparticles with either ionic or metallic character.

Alternatively, metals can simply be precipitated on the surface and in the pores of the molecular sieve. In the case where nanoparticles are preferred, consecutive treatment in e.g. a reductive atmosphere can be useful. In other cases, it may also be desirable to calcine the material after introduction of metals or metal ions.

The molecular sieve of the catalyst according to the invention is particularly useful in heterogeneous catalytic conversion reactions, such when the molecular sieve catalyzes the reaction of molecules in the gas phase or liquid phase.

It can also be formulated for other commercially important non-catalytic applications such as separation of gases.

The catalyst of the invention can be formed into a variety of physical shapes useful for specific applications. For example, the catalyst can be used in powder form or be shaped into pellets, extrudates or moulded forms, e.g. as full body corrugated catalyst.

In shaping the catalyst, it will typically be useful to apply additional organic or inorganic components. For catalytic applications it is particularly useful to apply a combination with alumina, silica, titania, various spinel structures and other oxides or combinations thereof. It may also be formulated with other active compounds such as active metals or other molecular sieves etc.

The catalyst can also be employed coated onto or introduced into a substrate that improves contact area, diffusion, fluid and flow characteristics of the gas stream. The substrate can be a metal substrate, an extruded substrate or a corrugated substrate made of ceramic paper. The substrate can be designed as a flow-through design or a wall-flow design. In the latter case the gas flows through the walls of the substrate, and in this way, it can also contribute with an additional filtering effect.

The catalyst is typically present on or within the substrate in amounts between 10 and 600 g/L, preferably 100 and 300 g/L, as calculated by the weight of the catalyst per volume of the total catalyst article.

The catalyst is coated on or introduced into the substrate using known wash-coating or impregnation techniques. Thereby, a catalyst powder is suspended in liquid media together with binder(s) and stabilizer(s). The wash coat can then be applied on the surfaces and walls of the substrate. The wash coat optionally also contains binders based on $TiO_2$, $SiO_2$, $Al_2O_3$, $ZrO_2$, $CeO_2$ and combinations thereof.

The catalyst can also be applied as one or more layers on a substrate in combination with other catalytic functionalities or other molecular sieve/zeolite catalysts. One specific combination is a layer with an oxidation catalyst containing for example platinum or palladium or combinations thereof. The catalyst can be additionally applied in limited zones along the gas-flow-direction of the substrate.

The catalyst according to the invention is in particular useful as mentioned hereinbefore, in catalytic conversion of oxides of nitrogen, typically in the presence of oxygen. In particular, the catalyst can be used in the selective catalytic reduction (SCR) of oxides of nitrogen with a reductant such as ammonia and precursors thereof, including urea. The reductant can also be one or more hydrocarbons.

For this type of application, the molecular sieve of the catalyst will typically be loaded with a transition metal such as copper or iron or combinations thereof, using any of the procedures described above, in an amount sufficient to catalyse the specific reaction.

In certain aspects of the invention a certain amount of alkali or earth alkali in the molecular sieve of the catalyst can be beneficial. See for example a description of alkali and earth alkali effects on copper promoted CHA in [F. Gao, Y. Wang, N. M. Washton, M. Kollár, J. Szanyi, C. H. F. Peden, *ACS Catal.* 2015, 5, 6780-6791] and beneficial role for low silica-to-alumina ratio conventional CHA molecular sieves without disorder disclosed in US Patent application US20150078989 A1.

In other applications, it may be preferred that the molecular sieve of the catalyst is essentially free of alkali or earth alkali.

It has been observed that the disordered molecular sieve of the catalyst according to an embodiment of the invention loaded with copper, provides higher NOx conversion than a pure CHA zeolite loaded with copper in the selective catalytic reduction of nitrogen oxides using ammonia as a reductant. Furthermore, a higher NOx conversion is retained after severe hydrothermal aging for the disordered molecular sieve according to the present invention compared to pure CHA loaded with copper.

When used in a method for the removal of nitrogen oxides, the catalyst comprising the molecular sieve according to the invention can advantageous be used in the reduction of nitrogen oxides in exhaust from a vehicular (i.e. mobile) internal combustion engine or exhaust or off-gas from a stationary source.

In these applications, an exhaust gas cleaning system can comprise one or more of the following components: a diesel oxidation catalyst (DOC), a diesel particulate filter (DPF), a selective catalytic reduction catalyst (SCR) and/or an ammonia slip catalyst (ASC). Such a system also typically comprises means for metering a reductant as well as hydrocarbons into the exhaust gas system upstream the SCR and DOC, respectively.

Preferably, the SCR catalyst consists of or comprises the catalyst of the invention. The SCR catalyst may also contain other active components such as other molecular sieves. When the SCR catalyst is arranged in the exhaust gas cleaning system, the catalyst is exposed to high temperatures either by the exhaust gas from the engine or during thermal regeneration of one or more of the components in the system.

In the exhaust gas cleaning system as described above, the SCR catalyst, can be arranged between the DPF and the ASC components. Another possibility is to arrange the SCR catalyst up-stream of the DOC, where some tolerance to unburnt hydrocarbons is required. The SCR catalyst may also be included in the DPF or combined with the ASC into a single component with a dual function.

As mentioned hereinbefore, the catalyst according to the invention can also be part of an ammonia slip catalyst (ASC). The ASC catalyst is used in combination with the catalyst, and its function is to remove excess amount of ammonia that is employed in the SCR stage to remove high amounts of nitrogen oxides from the exhaust gas.

ASC-type catalysts are bifunctional catalysts. The first function is oxidation of ammonia with oxygen, which produces NOx, and the second function is NH3-SCR, in which NOx and residual amounts of ammonia react to nitrogen.

Hence, ASC catalysts consist of a combination of a catalyst active for the oxidation of ammonia by oxygen and a component active for NH3-SCR.

The most commonly applied catalysts for the oxidation of ammonia by oxygen are based on metals like Pt, Pd, Rh, Ir, Ru, but transition metal oxides or a combination of metal oxides, for example oxides Ce, Ti, V, Cr, Mn, Fe, Co, Nb, Mo, Ta, W can also be used for this purpose. When such catalysts are combined, the catalyst according to the invention, preferably loaded with copper and/or iron, provides an improved ammonia slip catalyst.

The ammonia slip catalysts as disclosed above can also include auxiliary materials, for example binders and support materials for the noble metal components, such as Al2O3, TiO2, SiO2. Such combinations can have different forms, such as a mixture of the ammonia oxidation catalyst with the SCR-active form of the catalyst according to the invention, reactors or catalyst items in series (See examples in U.S. Pat. No. 4,188,364).

In particular, the ammonia slip catalyst can be a washcoated layer of a mixture of the ammonia oxidation catalyst with the SCR-active form of the catalyst of the invention on a monolith, or a multi-layered arrangement washcoated on a monolith (JP3436567, EP1992409), in which the different layers contain different amounts of the ammonia oxidation component, or of the SCR-active form of the catalyst according to the invention, or of any combination of the ammonia oxidation component and the SCR-active form of the catalyst of the invention.

In another configuration, the ammonia oxidation catalyst, or the SCR-active form of the catalyst of the invention, or any combination of the ammonia oxidation catalyst and the SCR-active form of the catalyst is present in walls of a monolith (JP3793283). This configuration can further be combined with different combinations of washcoated layers.

Another configuration of the ASC catalyst is monolithic catalyst article with an inlet end and an outlet end, in which the inlet end contains an ammonia oxidation catalyst, or the SCR-active form of catalyst of the invention, or any combination of the ammonia oxidation catalyst and SCR-active form of the catalyst of the invention that is different to the ammonia oxidation catalyst, or SCR-active form of the molecular sieve of the invention, or any combination of the ammonia oxidation component and SCR-active form of the catalyst according to the invention at the outlet end (U.S. Pat. No. 8,524,185).

Another use of the catalyst according to the invention is application in the reduction of nitrogen oxides in the exhaust gas from a gas turbine using ammonia or a precursor thereof as a reductant as mentioned hereinbefore. In this application, the catalyst can be arranged directly downstream of the gas turbine and is exposed to large temperature fluctuations during gas turbine start-up and shut-down procedures.

In certain applications, the catalyst of the invention is used in a gas turbine system with a single cycle operational mode without any heat recovery system down-stream of the turbine. When placed directly after the gas turbine the catalyst is able to withstand exhaust gas temperatures up to 650° C. with a gas composition containing water.

Further applications of the catalyst according to the invention are in a gas turbine exhaust treatment system in combination with a heat recovery system such as a Heat Recovery System Generator (HRSG). In such a process layout, the catalyst is arranged between the gas turbine and the HRSG. The catalyst can be also arranged in several locations inside the HRSG.

When used in the abatement of hydrocarbons and carbon monoxide in exhaust or off-gases the catalyst according to the invention is typically combined with an oxidation catalyst. The oxidation catalyst, typically composed of precious metals, such as Pt and Pd, can e.g. be placed either up-stream or down-stream of the catalyst according to the invention or both inside and outside of e.g. the HRSG in gas turbine system. The oxidation functionality can also be combined with the catalyst into a single catalytic unit.

The oxidation functionality can be combined directly with the molecular sieve by using the molecular sieve of the catalyst as support for the precious metals. The precious metals can also be supported onto another support material and physically mixed with the molecular sieve.

The catalyst according to the invention is capable of removing nitrous oxide. In this application, the catalyst can for example be arranged in combination with a nitric acid production loop in a primary, secondary or a tertiary abatement setup. In such an abatement lay out, the catalyst can be used to remove nitrous oxide as well as nitrogen oxides as separate catalytic articles or combined into a single catalytic article. The nitrogen oxide may be used to facilitate the removal of the nitrous oxide. Ammonia or lower hydrocarbons, including methane, may also be added as a reductant to further reduce nitrogen oxides and/or nitrous oxide.

When used in the conversion of oxygenates into various hydrocarbons by means of the catalyst according to the invention, the feedstock of oxygenates is typically lower alcohols and ethers containing one to four carbon atoms and/or combinations thereof. The oxygenates can also be or comprise carbonyl compounds such as aldehyde, ketones and carboxylic acids. Particularly suitable oxygenate compounds are methanol, dimethyl ether, and mixtures thereof. Such oxygenates can be converted into hydrocarbons in presence of the catalyst. In such an application, the oxygenate feedstock is typically diluted and the temperature and space velocity is controlled to obtain the desired product range.

A further application of the catalyst of the invention is in the production of lower olefins e.g. suitable for addition to a gasoline pool. In this application, the product range can be rich in aromatic compounds. The molecular sieve of the catalyst is thereby preferably in its acidic form and will be extruded with binder materials or shaped into pellets together with suitable matrix and binder materials as described above. Other suitable active compounds such as metals and metal ions may also be included to change the selectivity of the catalyst towards the desired product range.

The catalyst of the invention is, as mentioned hereinbefore is additionally useful in the partial oxidation of methane to methanol or other oxygenated compounds such as dimethyl ether.

One example of a process for the direct conversion of methane into methanol at temperatures below 300° C. in the gas phase is provided in WO11046621A1.

When used in the partial oxidation of methane to methanol or other oxygenated compounds, the molecular sieve of the catalyst of the invention is loaded with an amount of copper sufficient to carry out the conversion. Typically, the catalyst will be treated in an oxidizing atmosphere whereafter methane is subsequently passed over the activated catalyst to directly form methanol. Subsequently, the produced methanol can be extracted by suitable methods and the active sites regenerated by another oxidative treatment. An increase or a continuous production of methanol is achieved by addition of water to the reactant stream to continuously extract methanol without having to alter the conditions between oxidative treatments and methanol formation.

The catalyst according to the invention can further be used in isomerization, cracking and hydrocracking and other reactions for upgrading oil.

It may also be used as a hydrocarbon trap e.g. from cold-start emissions from various engines.

Furthermore, it can be used for the preparation of lower amines such as methyl amine and dimethylamine by reaction of ammonia with methanol.

EXAMPLES

Example 1

Preparation of ABC-6 Aluminosilicate with Approximate 5% Disorder in the CHA-GME Series A mixture of 18.08 g tetraethylammonium hydroxide (35 wt. % aqueous solution), 6.88 g sodium hydroxide (25 wt. % aqueous solution), 15.45 g FAU zeolite ($SiO_2/Al_2O_3=16$) and 59.58 g water was prepared.

Figure 2:
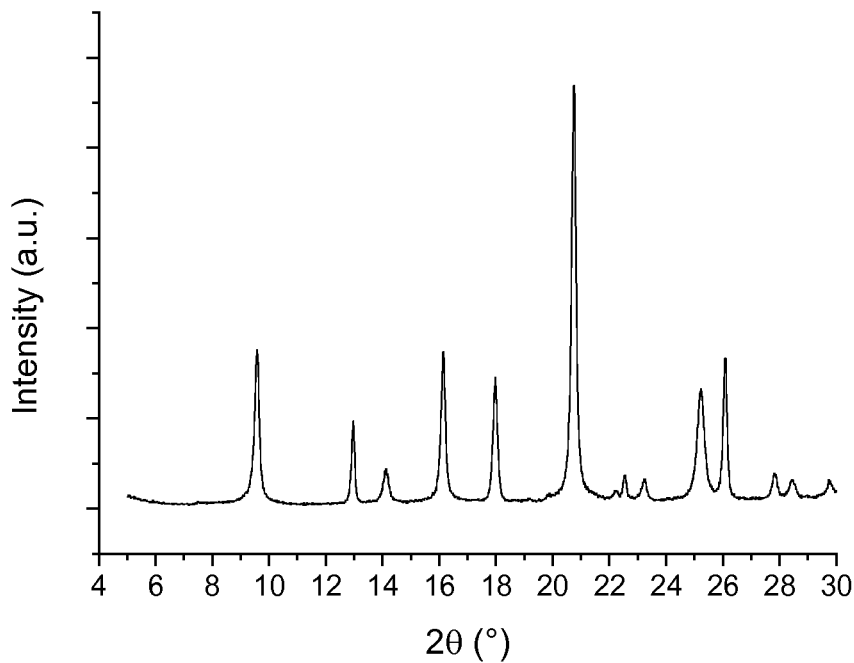
FIG. 2 is an XRPD of the as-prepared molecular sieve prepared in Example 1 with approximate 5% disorder in the CHA-GME series (see FIG. 1)

The mixture was heated in a closed Teflon lined autoclave at 150° C. for two days and the solid product separated by filtration and afterwards washed with deionized water. The X-ray diffraction pattern of the dried product is shown in FIG. 2 and indicates and approximate 5% disorder in the CHA-GME series.

Figure 3:
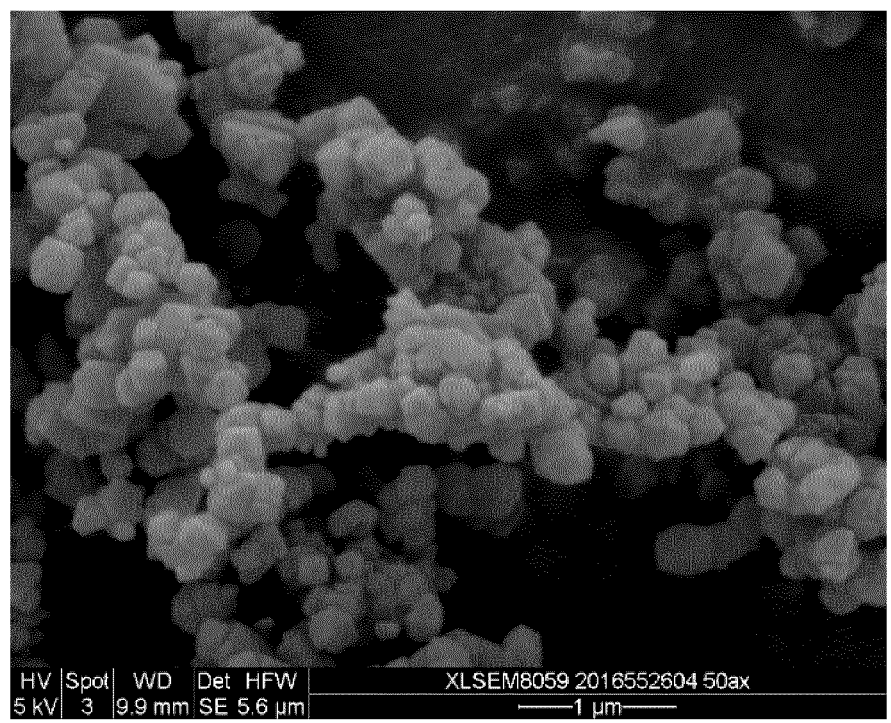
FIG. 3 is a Scanning Electron Microscopy (SEM) image of the as-synthesized molecular sieve prepared in Example 1.

The product had a silica-to-alumina mole ratio of 12.0 as determined by ICP elemental analysis. The SEM image (FIG. 3) shows that the crystal morphology is predominantly hexagonal bipyramidal.

Figure 4:
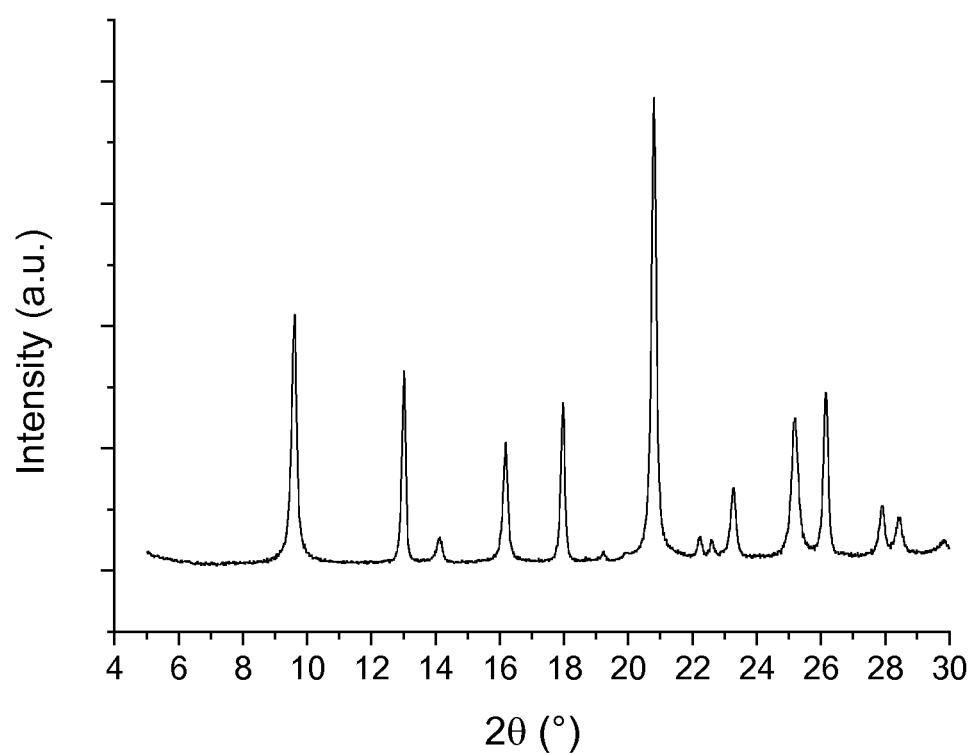
FIG. 4 is an XRPD of the calcined molecular sieve prepared in Example 1.

The as-synthesized product was calcined at 580° C. The powder XRD pattern (FIG. 4) indicated that the material remains stable after calcination to remove the remaining organic structure directing agent.

Example 2

Preparation of ABC-6 Aluminosilicate with Approximate 20% Disorder in the CHA-GME Series A mixture of 26.08 g tetraethylammonium hydroxide (35 wt. % aqueous solution), 9.92 g sodium hydroxide (25 wt. % aqueous solution), 14.86 g FAU zeolite ($SiO_2/Al_2O_3=16$) and 49.15 g water was prepared.

Figure 5:
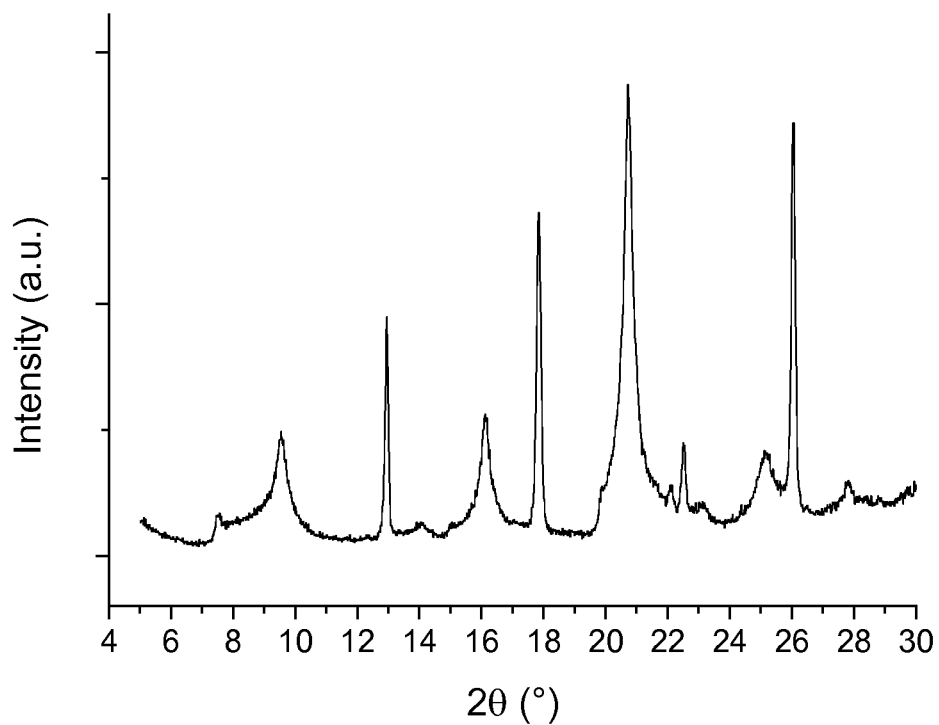
FIG. 5 is an XRPD of material prepared in Example 2 with approximate 20% disorder in the CHA-GME series (see FIG. 1)

The mixture was heated in a closed Teflon lined autoclave at 150° C. for two days and the solid product separated by filtration and afterwards washed with deionized water. The X-ray diffraction pattern of the dried product is shown in FIG. 5 and indicates and approximate 20% disorder in the CHA-GME series.

Figure 6:
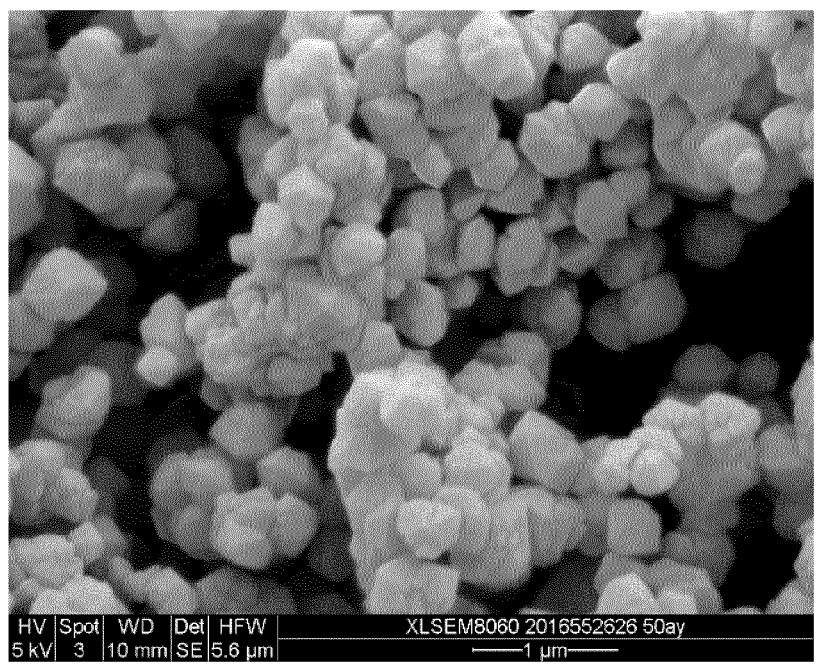
FIG. 6 is a Scanning Electron Microscopy (SEM) image of the as-synthesized molecular sieve prepared in Example 2.

The product had a silica-to-alumina mole ratio of 9.1 as determined by ICP elemental analysis. The SEM image (FIG. 6) shows that the crystal morphology is predominantly hexagonal bipyramidal and capped bipyramidal.

Figure 7:
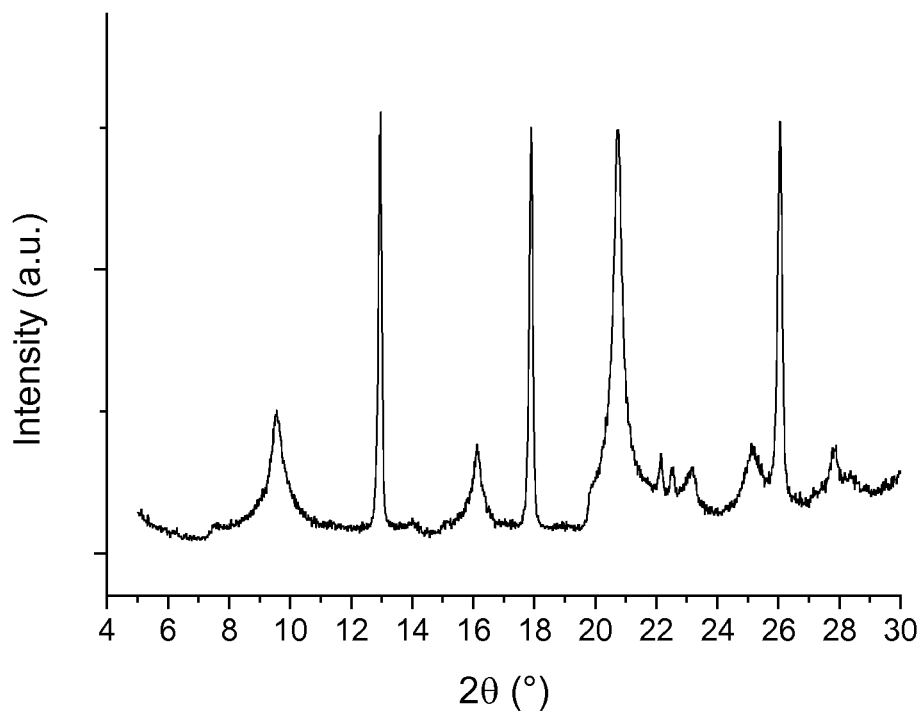
FIG. 7 is an XRPD of the calcined molecular sieve prepared in Example 2.

The as-synthesized product was calcined at 580° C. The powder XRD pattern (FIG. 7) indicated that the material remains stable after calcination to remove the remaining organic structure directing agent.

Example 3

Preparation of ABC-6 Aluminosilicate with Approximate 40% Disorder in the CHA-GME Series A mixture of 33.74 g tetraethylammonium hydroxide (35 wt. % aqueous solution), 9.62 g sodium hydroxide (25 wt. % aqueous solution), 14.42 g FAU zeolite ($SiO_2/Al_2O_3=16$) and 42.22 g water was prepared. The mixture was heated in a closed Teflon lined autoclave at 150° C. for two days and the solid product separated by filtration and afterwards washed with deionized water.

Figure 8:
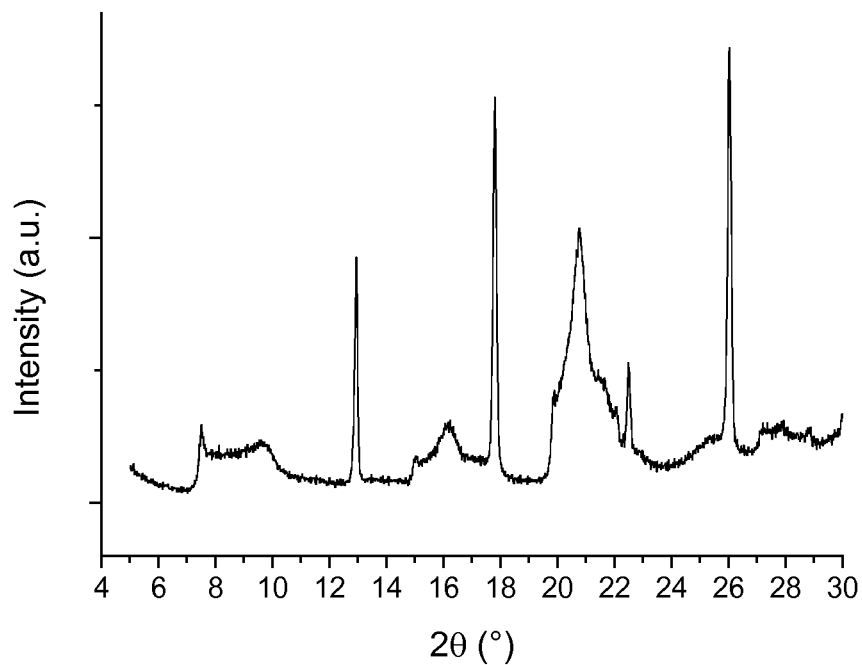
FIG. 8 is an XRPD of material prepared in Example 3 with approximate 40% disorder in the CHA-GME series (see FIG. 1)

The X-ray diffraction pattern of the dried product is shown in FIG. 8 indicates an approximate 40% disorder in the CHA-GME series.

Figure 9:
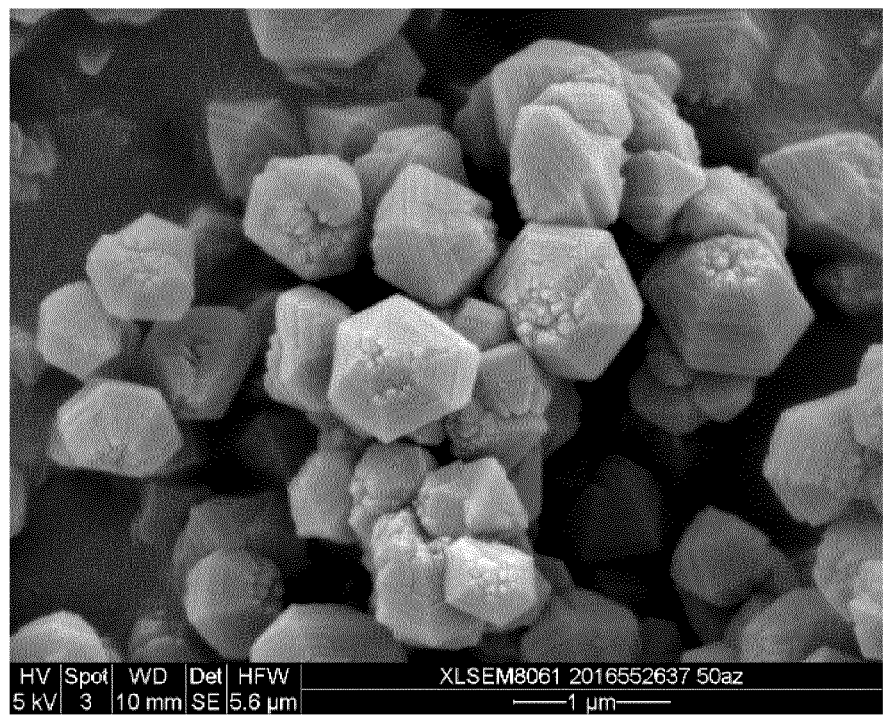
FIG. 9 is a Scanning Electron Microscopy (SEM) image of the as-synthesized molecular sieve prepared in Example 3.

The product had a silica-to-alumina mole ratio of 8.3 as determined by ICP elemental analysis. The SEM image (FIG. 9) shows that the crystal morphology is predominantly hexagonal capped bipyramidal.

Figure 10:
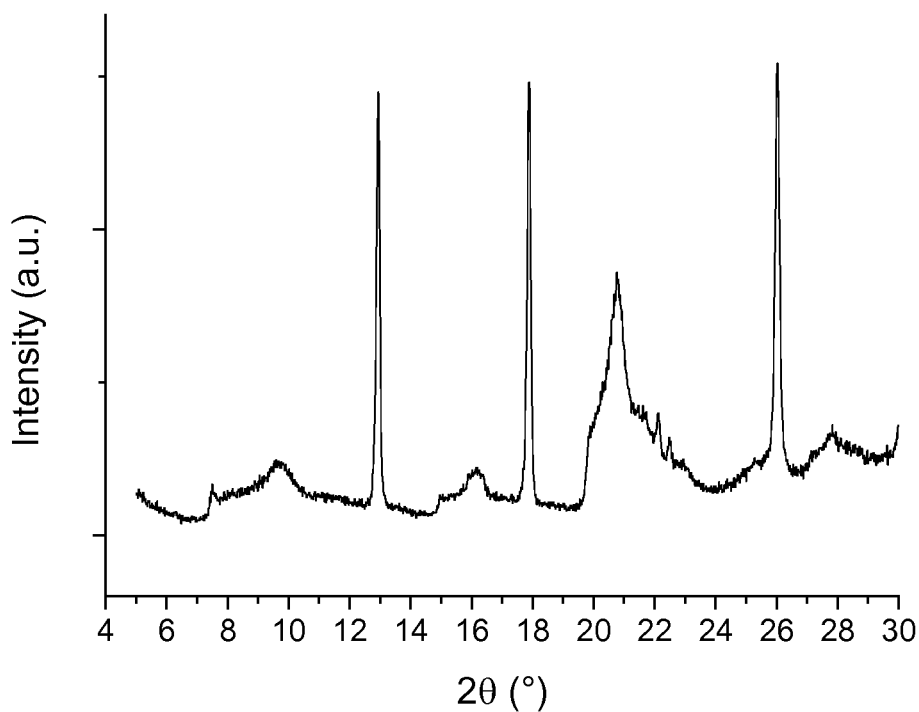
FIG. 10 is an XRPD of the calcined molecular sieve prepared in Example 3.

The as-synthesized product was calcined at 580° C. The powder XRD pattern (FIG. 10) indicates that the material remains stable after calcination to remove the remaining organic structure directing agent.

Example 4

Preparation of ABC-6 Aluminosilicate with Approximate 70% Disorder in the CHA-GME Series A mixture of 33.47 g tetraethylammonium hydroxide (35 wt. % aqueous solution), 12.72 g sodium hydroxide (25 wt. % aqueous solution), 14.30 g FAU zeolite ($SiO_2/Al_2O_3=16$) and 39.50 g water was prepared.

Figure 11:
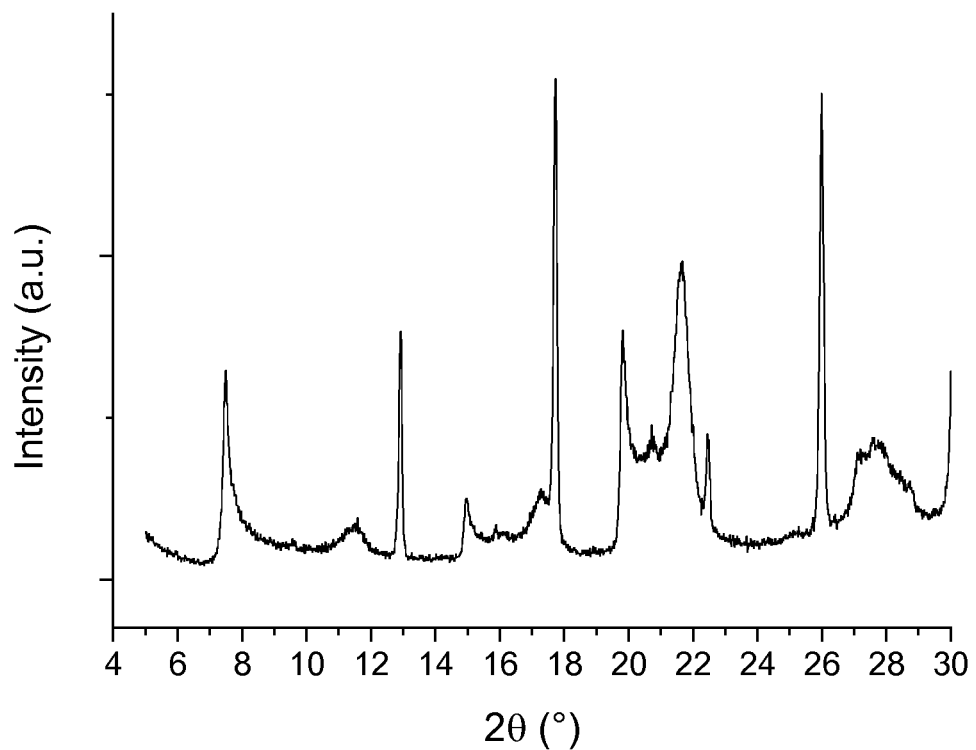
FIG. 11 is an XRPD of material prepared in Example 4 with approximate 70% faulting probability in the CHA-GME series (see FIG. 1)

The mixture was heated in a closed Teflon lined autoclave at 150° C. for two days and the solid product separated by filtration and afterwards washed with deionized water. The X-ray diffraction pattern of the dried product is shown in FIG. 11 and indicates and approximate 70% disorder in the CHA-GME series.

Figure 12:
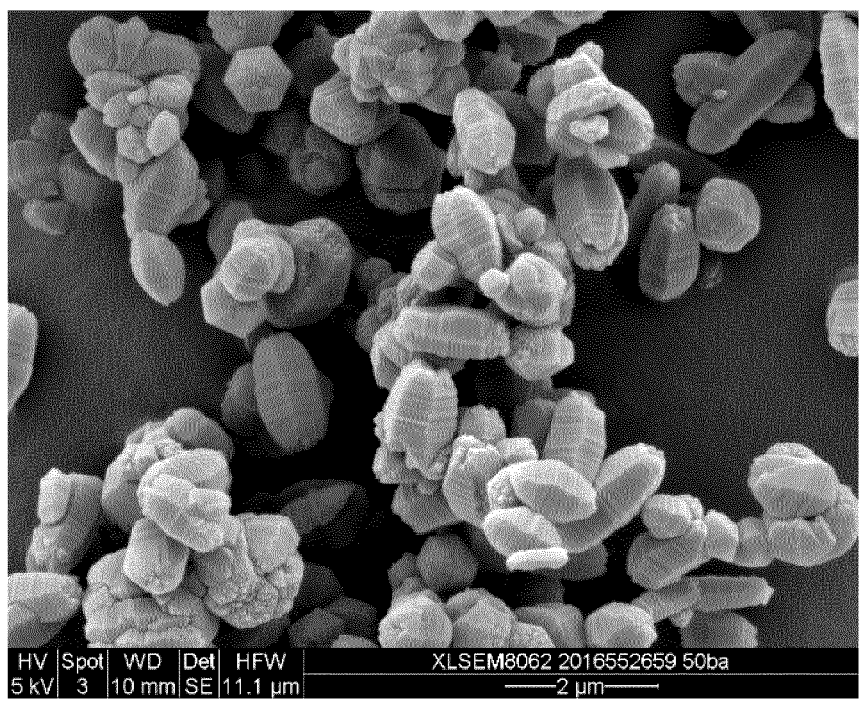
FIG. 12 is a Scanning Electron Microscopy (SEM) image of the as-synthesized molecular sieve prepared in Example 4.
Figure 13:
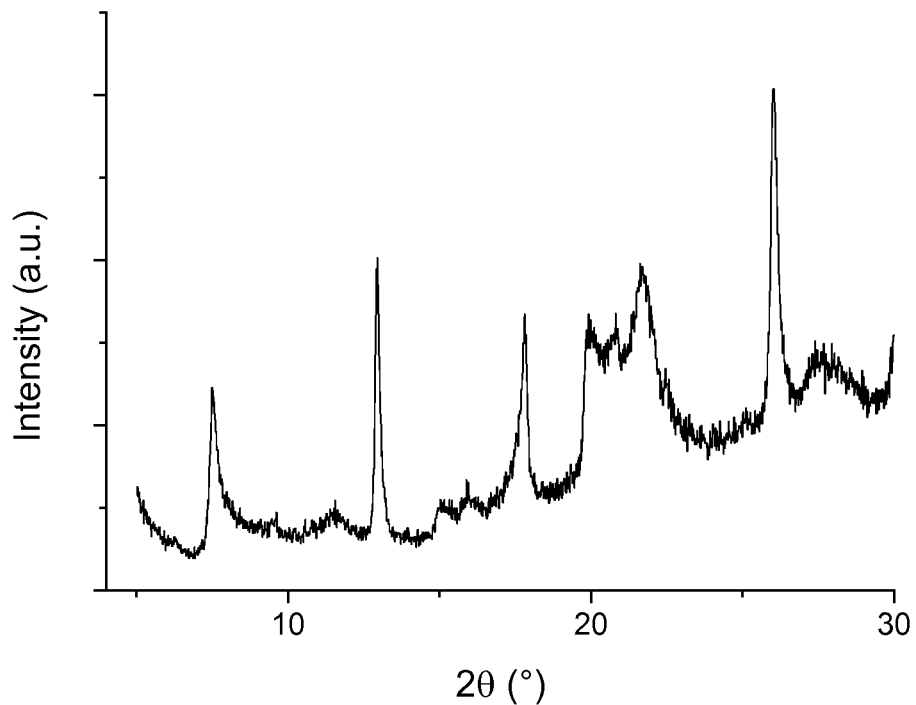
FIG. 13 is an XRPD of the calcined molecular sieve prepared in Example 4.

The product had a silica-to-alumina mole ratio of 6.5 as determined by ICP elemental analysis. The SEM image (FIG. 12) shows that the crystal morphology is predominantly elongated hexagonal capped bipyramidal The as-synthesized product was calcined at 580° C. The powder XRD pattern (FIG. 13) indicated that the material remains substantial stable after calcination to remove the remaining organic structure directing agent.

Examples 5-12

Use of Different FAU-Sources and Other Si- and Al-Sources

This set of examples show that various crystalline molecular sieves can be used in the preparation of the disordered CHA-GME molecular sieve with high silica-to-alumina ratios. Furthermore, the examples illustrate how other sources of silica and alumina can also be used in combination with a crystalline molecular sieve.

The general procedure described in Example 1 was repeated using: different FAU zeolites in the synthesis mixture with different silica-to-alumina ratios (SAR), using a combination of a FAU zeolites and an other sources of silica- and alumina as summarized in Table 5, together with the obtained product phases, silica-to-alumina ratios and amount of stacking disorder Composition and product characteristics from Example 1-4 are also included.

For comparison a reference Cu-CHA (SiO2/Al2O3=14) was also tested.

Figure 14:
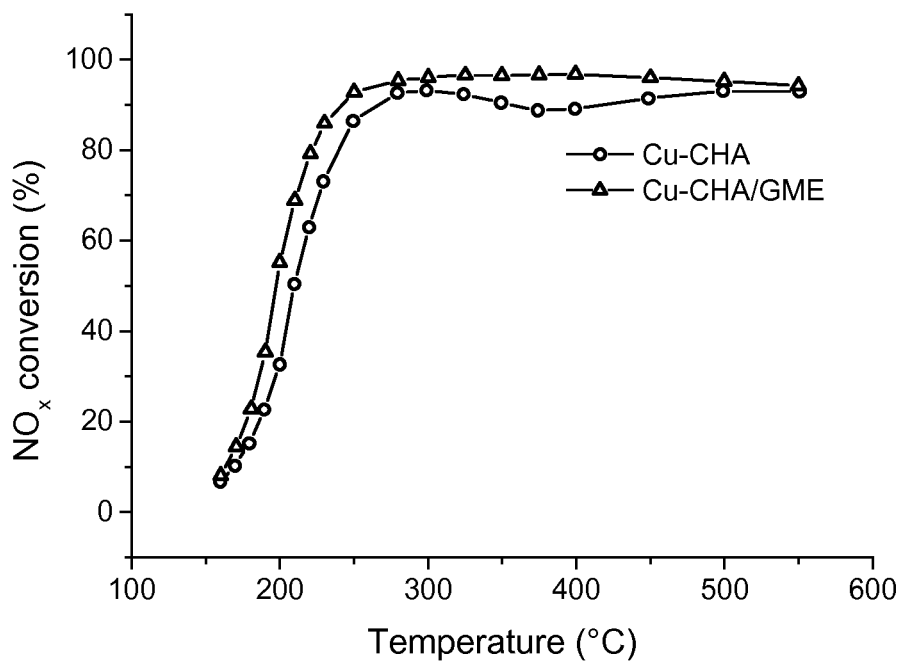
FIG. 14 shows measured NOx conversion in presence of fresh (non-aged) copper loaded molecular sieve prepared according to Example 2 and in presence of reference Cu-CHA.

FIG. 14 shows measured NOx conversion over fresh (non-aged) copper loaded molecular sieve prepared according to Example 2 and the reference Cu-CHA catalyst.

After the measurement of NOx conversion, the temperature was raised to 700° C. for 16 h in a gas containing 10% H2O and 10% O2, where-after the measurement of NOx conversion was repeated again. This is a measurement after severe hydrothermal aging.

Figure 15:
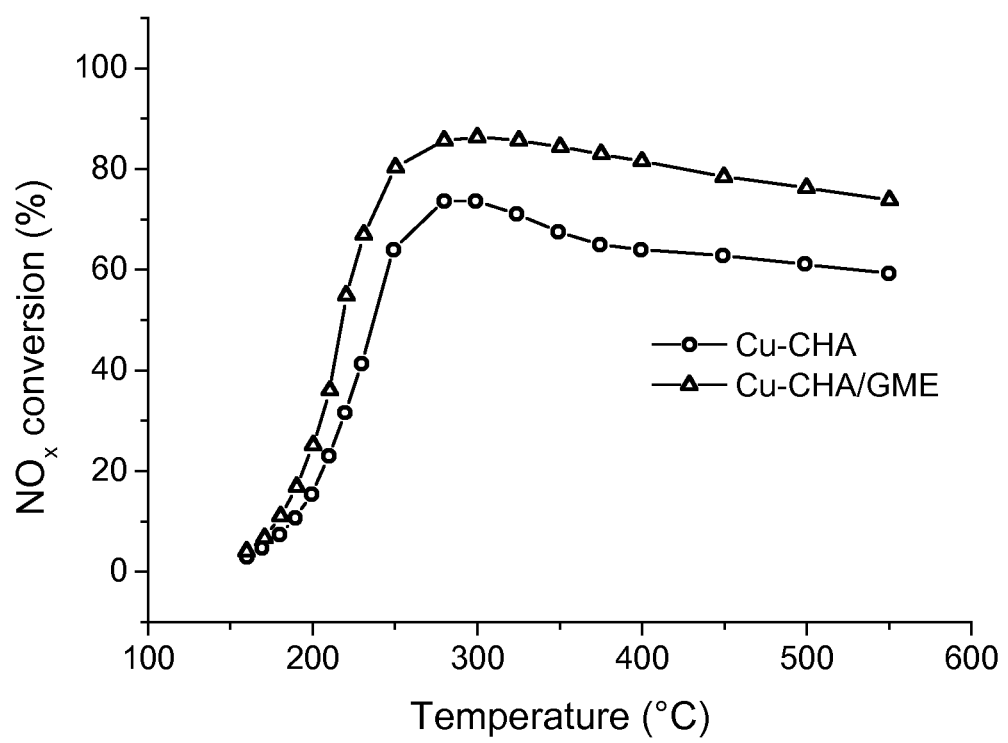
FIG. 15 shows measured NOx conversion in presence of aged (700° C. for 16 h in the presence of H2O) copper loaded molecular sieve prepared according to Example 2 and in presence of reference Cu-CHA.

FIG. 15 shows the measured NOx conversion over aged copper loaded molecular sieve after the described hydrothermal aging.

As evident from FIG. 14 and FIG. 15, the disordered molecular sieve according to the invention shows improved NOx conversion performance both in the fresh state and after severe hydrothermal aging despite the lower silica-to-alumina ratio of the copper-loaded disordered molecular sieve compared to the reference Cu-CHA.

The invention claimed is:

1. Catalyst for heterogeneous catalytic conversion reactions, comprising a molecular sieve belonging to the ABC-6 framework family with disorder in the ABC stacking sequence essentially composed of double-six-ring periodic

TABLE 5

| | Initial gel composition | | | | | Product characteristics | | |
|---|---|---|---|---|---|---|---|---|
| Ex. | SiO2/Al2O3 | OSDA/SiO2 | A/SiO2 | H2O/SiO2 | Al and Si-source$^a$ | Cryst. | Phase | SiO2/Al2O3 | Stacking disorder (%) |
| 1 | 16 | 0.20 | 0.20 | 20 | FAU (SAR = 16) | 150° C., 2 days | CHA-GME | 12.0 | 5 |
| 2 | 16 | 0.30 | 0.30 | 20 | FAU (SAR = 16) | 150° C., 2 days | CHA-GME | 9.1 | 20 |
| 3 | 16 | 0.40 | 0.30 | 20 | FAU (SAR = 16) | 150° C., 2 days | CHA-GME | 8.3 | 40 |
| 4 | 16 | 0.30 | 0.40 | 20 | FAU (SAR = 16) | 150° C., 2 days | CHA-GME | 6.5 | 70 |
| 5 | 30 | 0.50 | 0.20 | 25 | FAU (SAR = 30) | 140° C., 7 days | CHA-GME | 18.5 | 5 |
| 6 | 30 | 0.37 | 0.40 | 20 | FAU (SAR = 30) | 150° C., 2 days | CHA-GME | 10.4 | 10 |
| 7 | 20 | 0.40 | 0.40 | 20 | FAU (SAR = 20) | 150° C., 2 days | CHA-GME | 10.1 | 20 |
| 8 | 21 | 0.20 | 0.30 | 20 | FAU (SAR = 30) and ASA (SAR = 10) | 150° C., 2 days | CHA-GME | 10.2 | 5 |
| 9 | 21 | 0.30 | 0.40 | 20 | FAU (SAR = 30) and ASA (SAR = 10) | 150° C., 2 days | CHA-GME | 10.2 | 50 |
| 10 | 16 | 0.20 | 0.30 | 20 | FAU (SAR = 5.2) + AS | 150° C., 2 days | CHA-GME + traces of GIS | — | — |
| 11 | 16 | 0.40 | 0.30 | 20 | 10% CHA (SAR = 14) + ASA (SAR = 16) | 150° C., 2 days | CHA-GME | — | 40 |
| 12 | 28 | 0.40 | 0.30 | 20 | FAU (SAR = 30) + CHA (SAR = 14) | 150° C., 2 days | CHA-GME | — | 2 |

$^a$FAU = FAU-zeolite, ASA = amorphous silicaalumina, AS = amorphous silica

Example 13

NOx Conversion and Hydrothermal Stability

The calcined product of example 2 was ion-exchanged four consecutive times with NH4Cl to remove the sodium cations. Afterwards the disordered molecular sieve in its NH4-form was ion-exchanged with an aqueous solution of copper(II)acetate and calcined at 500° C.

To determine NOx conversion, 5 mg of the copper-containing molecular sieve was heated in a U-shaped microreactor for 1 h at 550° C., and exposed to a total flow of 225 NmL/min of a gas containing 500 ppm NO, 533 ppm NH3, 5% H2O, and 10% O2 in N2.

The catalyst was then stepwise cooled to 160° C. using the same flow and gas composition. In each step the NOx conversion was determined by measuring the outlet concentrations.

building units and having a mole ratio of silicon oxide to aluminum oxide from about 8 to about 60,
  wherein the molecular sieve belongs to the disordered CHA-GME series, and
  wherein the calcined form of the molecular sieve has a powder X-ray diffraction pattern collected in Bragg-Brentano geometry with a variable divergence slit using Cu K-alpha radiation essentially as shown in the following table:

| 2-Theta (°) | d-spacing (Å) | Relative peak area | Peak character |
|---|---|---|---|
| 7.45-7.54 | 11.85-11.72 | W-M | Broad to sharp |
| 9.55-9.65 | 9.24-9.15 | VS-W | Sharp to broad |
| 11.40-11.66 | 7.75-7.58 | W-M | Broad to sharp |

| 2-Theta (°) | d-spacing (Å) | Relative peak area | Peak character |
|---|---|---|---|
| 12.90-13.04 | 6.85-6.78 | VS-M | Sharp |
| 14.07-14.21 | 6.29-6.23 | W | Sharp to broad |
| 14.89-15.12 | 5.94-5.85 | W | Broad to sharp |
| 16.08-16.27 | 5.50-5.44 | VS-W | Sharp to broad |
| 17.17-17.34 | 5.16-5.11 | W-S | Broad to sharp |
| 17.71-18.00 | 5.00-4.92 | VS-M | Sharp | where the relative areas of the observed peaks in the 2-Theta range 7-19 degrees are shown according to: W=weak: 0-20%; M=medium: 20-40%; S=strong: 40-60% and VS=very strong: 60-100%.

2. The catalyst according to claim 1, wherein the amount of stacking disorder of the molecular sieve is between 1 and 99%.

3. The catalyst according to claim 1, wherein crystals of the molecular sieve have a bipyramidal, elongated bipyramidal or capped bipyramidal morphology.

4. The catalyst according to claim 1, wherein the silica-to-alumina mole ratio of the molecular sieve is between 8 and 40.

5. The catalyst according to claim 1, wherein the silica-to-alumina mole ratio of the molecular sieve is between 10 and 20.

6. The catalyst according to claim 1, wherein at least a part of the aluminum and/or silicon of the molecular sieve is substituted by one or more metals selected from the group consisting of: tin, zirconium, titanium, hafnium, germanium, boron, iron, indium and gallium.

7. The catalyst according to claim 1, wherein the catalyst and/or the molecular sieve further comprises copper and/or iron.

8. A method for the conversion of nitrogen oxides to nitrogen in presence of a reductant comprising the step of contacting the nitrogen oxides and the reductant with the catalyst according to claim 1.

9. The method of claim 8, wherein the reductant comprises hydrocarbons and/or ammonia or a precursor thereof.

10. The method of claim 8, wherein the nitrogen oxides are contained in engine exhaust.

11. The method of claim 8, wherein the nitrogen oxides are contained in exhaust from a gas turbine.

12. The method of claim 8, wherein the nitrogen oxides comprise nitrous oxide.

13. A method for the selective oxidation of ammonia to nitrogen comprising the step of contacting the ammonia or a gas comprising the ammonia with the catalyst according to claim 1.

14. The method of claim 13, wherein the catalyst is combined with an oxidation functionality or catalyst.

15. The method of claim 13, wherein the catalyst is arranged downstream of a selective catalytic reduction catalyst and wherein an excess of ammonia is used to reduce nitrogen oxides.

16. A method for the simultaneous oxidation of hydrocarbons and carbon monoxide and the reduction of nitrogen oxides comprising the step of contacting the hydrocarbons, carbon monoxide and the nitrogen oxides with a catalyst according to claim 1.

17. The method of claim 16, wherein the catalyst further comprises one or more platinum group metals.

18. A method for the conversion of oxygenates to hydrocarbons comprising the step of contacting the oxygenates with a catalyst according to claim 1.

19. The method according to claim 18, wherein the hydrocarbons produced are primarily olefins.

20. A method for partial oxidation of methane to methanol and/or dimethyl ether comprising the step of contacting the methane with a catalyst according to claim 1.

* * * * *